United States Patent
Lu

(10) Patent No.: US 6,282,818 B1
(45) Date of Patent: Sep. 4, 2001

(54) POST-OPERATION SHOE

(76) Inventor: Lien-Tsung Lu, 8F-7, No. 155, Sec. 1, Keelung Road, Taipei City (TW)

( * ) Notice: Subject to any disclaimer, the term of this patent is extended or adjusted under 35 U.S.C. 154(b) by 0 days.

(21) Appl. No.: 09/610,039

(22) Filed: Jul. 5, 2000

(51) Int. Cl.$^7$ ............................. A43B 3/24; A43C 13/00
(52) U.S. Cl. ................................. 36/110; 36/100; 36/15
(58) Field of Search ................... 36/15, 100, 101, 36/110, 11.5

(56) References Cited

U.S. PATENT DOCUMENTS

| | | | |
|---|---|---|---|
| 1,463,514 | * 7/1923 | Lilienfeldt | 36/15 |
| 2,651,117 | * 9/1953 | Harris | 36/100 |
| 3,991,491 | * 11/1976 | Huang | 36/11.5 |
| 4,314,412 | * 2/1982 | Anderson et al. | 36/100 |
| 4,967,750 | * 11/1990 | Cherniak | 36/11.5 |
| 5,138,777 | 8/1992 | Darby . | |
| 5,491,909 | * 2/1996 | Darby | 36/110 |

FOREIGN PATENT DOCUMENTS

| | | | |
|---|---|---|---|
| 2263269 | * 3/1974 | (DE) | 36/101 |
| 2159038 | * 11/1985 | (GB) | 36/101 |
| 2178940 | * 2/1987 | (GB) | 36/101 |

\* cited by examiner

*Primary Examiner*—M. D. Patterson
(74) *Attorney, Agent, or Firm*—Marshall & Melhorn, LLC

(57) ABSTRACT

A post-operation shoe includes an outsole member having first and second end portions, an intermediate portion, an integral wedge member formed at a bottom side of the outsole member at the intermediate portion to be in contact with the ground. The wedge member is tapered in the longitudinal direction so that the second end portion is disposed higher than the first end portion. An upper includes an instep strap, an ankle strap, and left and right end portions extending downward from the instep strap and inserted between the outsole member and a midsole member which overlies and detachably connects with the outsole member via screws. The hook-and-loop fastener means is disposed on the left and right end portions and on one of the midsole and outsole members to releasably mount the upper on the sole, whereby the upper can be positioned to the sole interchangeably between a first position in which the ankle strap is located adjacent to the first end portion, and a second position in which the ankle strap is located adjacent to the second end portion.

5 Claims, 4 Drawing Sheets

POST-OPERATION SHOE

BACKGROUND OF THE INVENTION

1. Field of the Invention

The present invention relates to a post-operation shoe, more particularly to a post-operation shoe for elevating and supporting a post-operative or otherwise traumatized foot portion in order to remove pressure from the foot portion when the foot portion is the forefoot or the heel.

2. Description of the Related Art

When surgical operations have been done to a foot portion or when a foot portion is otherwise traumatized, the patient feels discomfort while walking due to the pressure applied on the traumatized foot portion. It is thus desirable to elevate the traumatized foot portion during walking so as to remove pressure therefrom and sooth the pain in the traumatized foot portion. U.S. Pat. No. 5,138,777 discloses a post-operative shoe which includes an upper assembly secured to a sole assembly, and a wedge undersole of triangular shape. The wedge undersole is integrated to a bottom surface of a midsole of the sole assembly, and ensures the top surface of the midsole to extend upwardly and forwardly in a direction toward the toe region of the shoe. This type of post-operative shoe help to relieve pressure on the forefoot, and is only suitable when the traumatized portion is at the forefoot.

It is thus desirable to provide a post-operation shoe which can be used for a foot which is traumatized at either the forefoot or the heel.

SUMMARY OF THE INVENTION

Therefore, the main object of the present invention is to provide a post-operation shoe for a foot which is traumatized at either the forefoot or the heel.

According to a first aspect of the present invention, a post-operation shoe includes a sole, a wedge member, an upper and hook-and-loop fastener means. The sole includes an outsole member and amidsole member, the outsole member having first and second end portions which are opposite to each other in a longitudinal direction, and an intermediate portion between the first and second end portions, the midsole overlying and releaseably connected to the outsole member. The wedge member is formed integrally with a bottom side of the outsole member at the intermediate portion, and has a flat bottom end face adapted to be in contact with the ground. The wedge member is tapered in the longitudinal direction so that the second end portion is disposed higher than the first end portion. The upper includes an instep strap, an ankle strap, and left and right end portions extending downward from the instep strap and inserted between the midsole and outsole members. The hook-and-loop fastener means is disposed on the left and right end portions and on one of the midsole and outsole members to releasably mount the upper on the sole, whereby the upper can be positioned to the sole interchangeably between a first position in which the ankle strap is located adjacent to the first end portion, and a second position in which the ankle strap is located adjacent to the second end portion.

According to a second aspect of the present invention, a post-operation shoe includes an elongate outsole member, a wedge member, an upper, a midsole member and a releasable connector. The outsole member has first and second end portions which are opposite to each other in a longitudinal direction, and an intermediate portion between the first and second end portions. The wedge member is secured to a bottom side of the outsole member at the intermediate portion, and has a flat bottom end face adapted to be in contact with the ground. The wedge member is tapered in the longitudinal direction so that the second end portion is disposed higher than the first end portion. The upper has an instep strap and an ankle strap. The midsole member is connected to the upper, and overlies the outsole member. The midsole has a heel portion beneath the ankle strap. The releasable connector is disposed on and interconnects the midsole and outsole members. The midsole member is detachable from the outsole member to change from a position in which the heel portion is located immediately above the first end portion, to another position in which the heel portion is located immediately above the second end portion, and vice versa.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
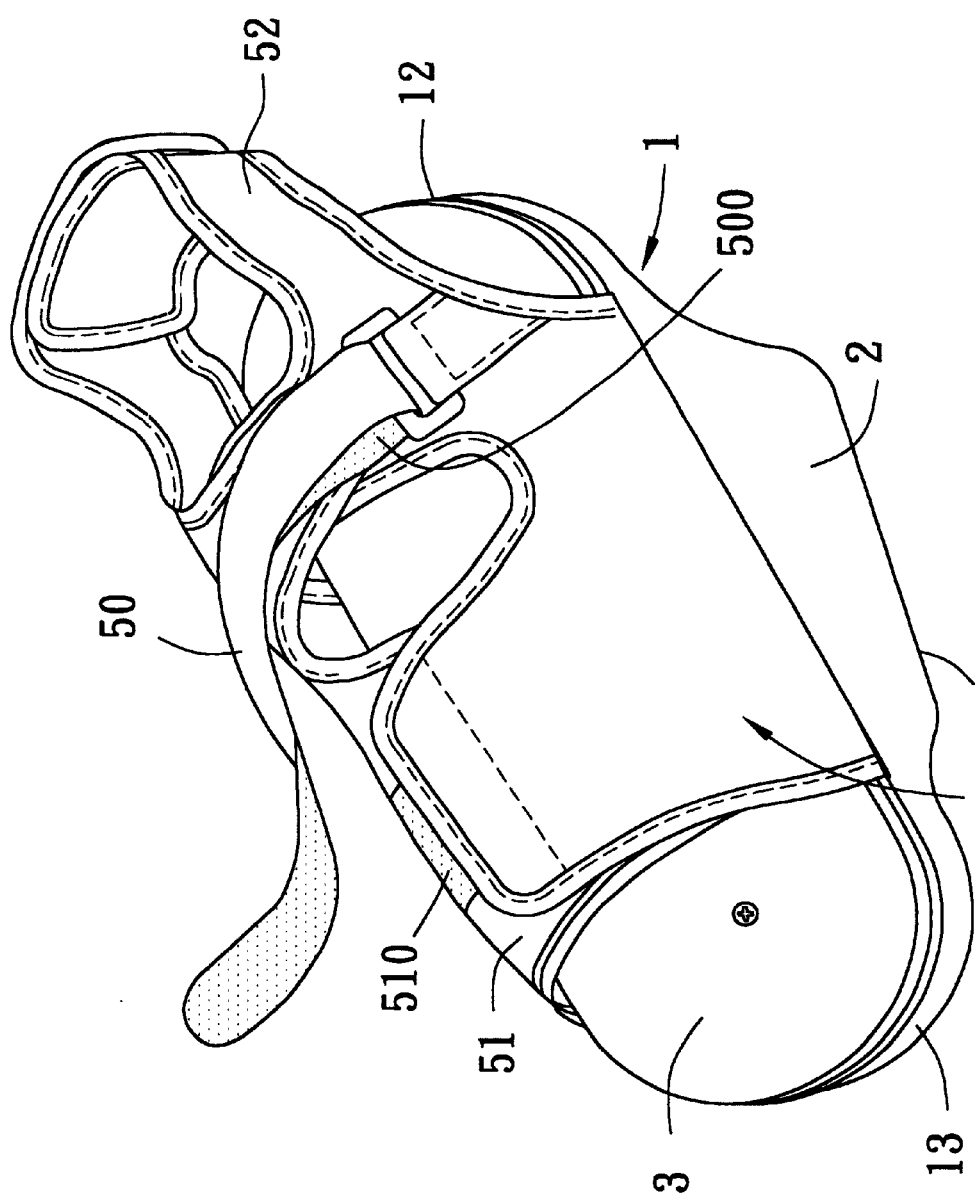
FIG. 1 is a perspective view of a preferred embodiment of a post-operation shoe of the present invention.
Figure 2:
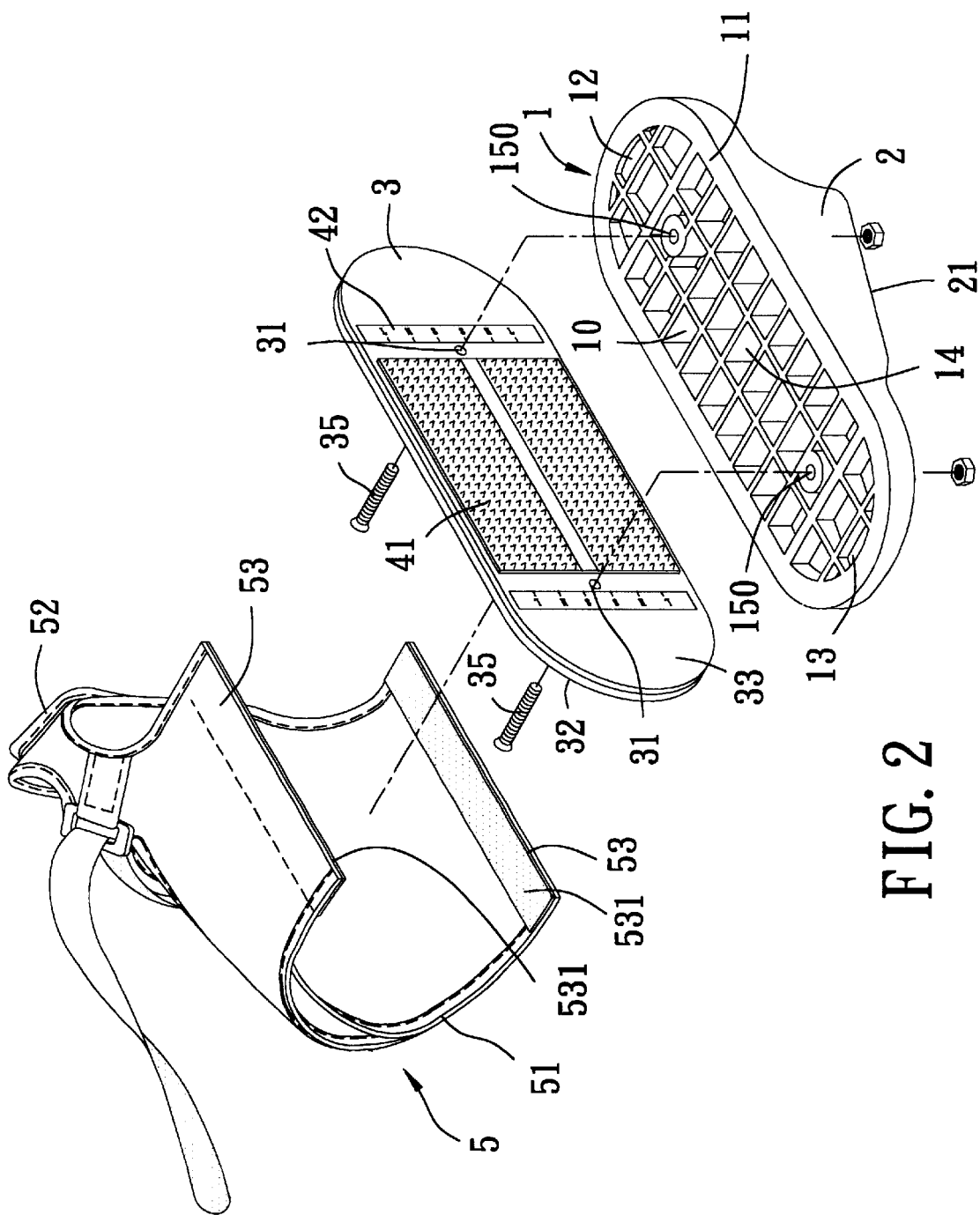
FIG. 2 is an exploded perspective view of the preferred embodiment.
Figure 3:
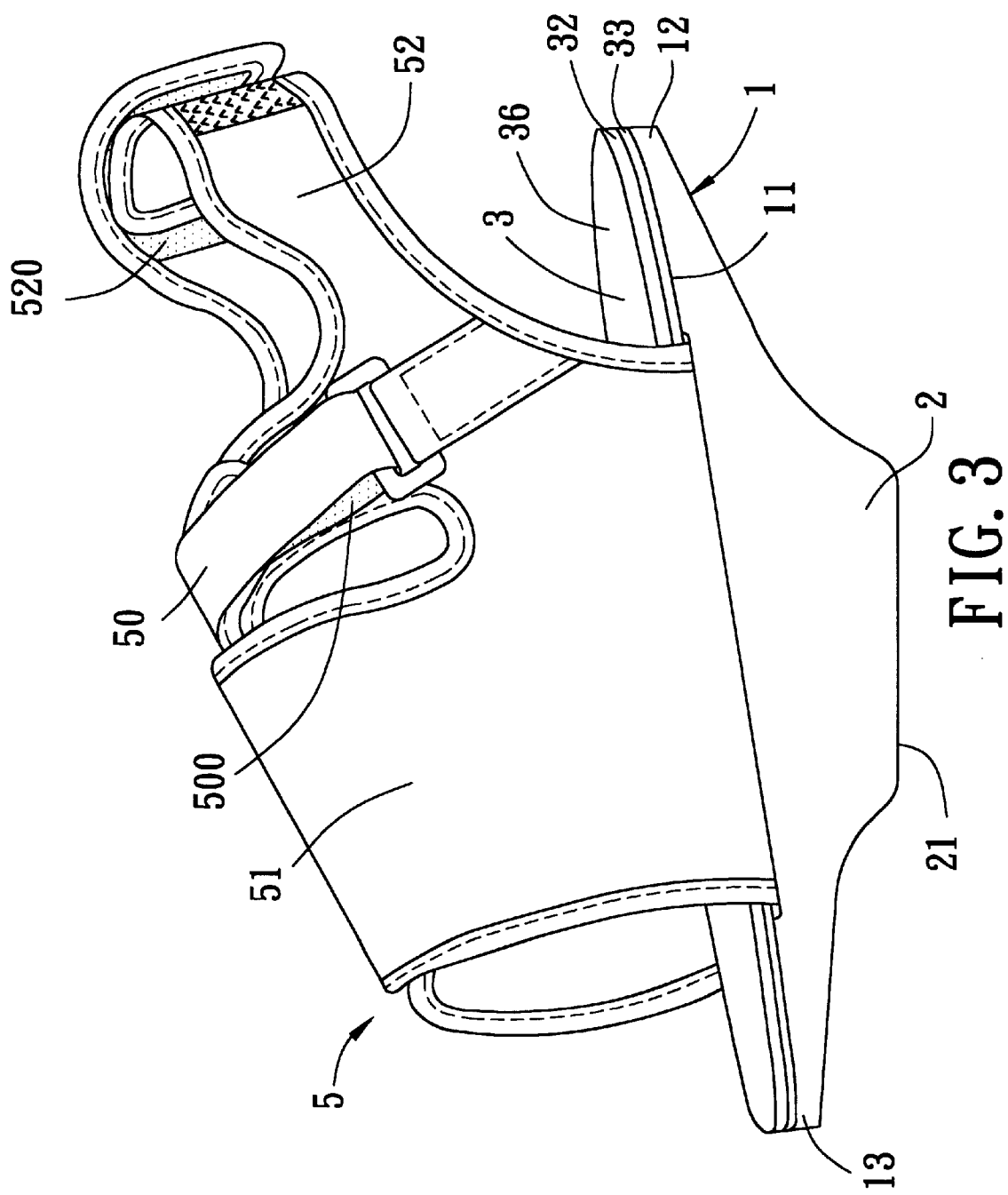
FIG. 3 is a side view of the preferred embodiment in a first mode of use.

Referring to FIGS. 1 to 3, the preferred embodiment of the post-operation shoe of the present invention is useful after foot surgery at either the forefoot or the heel, or for healing of the traumatized forefoot or heel. The post-operation shoe of the preferred embodiment is shown to include an elongate outsole member 1, an elongate midsole member 3 overlying the outsole member 1, an upper 5, and a wedge member 2 secured to a bottom side of the outsole member 1.

The outsole member 1 has first and second end portions 13, 12 which are opposite to each other in a longitudinal direction of the outsole member 1, and an intermediate portion 14 between the first and second end portions 13, 12. The outsole member 1 is formed with a plurality of cavities 10 to result in reduction of weight and material cost savings. Each of the first and second end portions 13, 12 has a screw hole 150 formed therethrough. The wedge member 2 is formed integrally with the outsole member 1 from a resilient rubber material, and has a flat bottom end face 21 adapted to be in contact with the ground. The wedge member 2 is tapered in the longitudinal direction so that the second end portion 12 of the outsole member 1 is disposed higher than the first end portion 13 when the bottom end face 21 of the wedge member 2 is in contact with the ground 13, and so that a top side 11 of the outsole member 1 is inclined relative to the ground by an angle of about 10°.

The midsole member 3 has a shape conforming with the top side 11 of the outsole member 1, and is formed with two fastener holes 31 which are aligned respectively with the screw holes 150 in the outsole member 1 for fastening detachably to the top side 11 of the outsole member 1 by means of two screws 35. The midsole member 3 and the outsole member 1 have a common line of symmetry which passes through intermediate portions thereof, and which is transverse to the longitudinal direction of the outsole member 1. The midsole member 3 includes upper insole layer 32 formed from a soft foam material, and a lower insole layer 33 formed from a rigid plastic material. The bottom side of the midsole member 3 is provided with a hook fastener unit 41 of a hook and loop fastener, and scale marks 42 on opposite front and rear sides of the hook fastener unit 41.

The upper 5 includes front and rear instep straps 51, 50 and an ankle strap 52 extending rearwardly from the front and rear instep straps 51, 50. The upper 5 is formed from left and right flaps which overlap each other and which are connected releasably to each other at the front and rear instep straps 51, 50 and the ankle strap 52 by means of hook and loop fasteners 510, 500, 520. The hook and loop fasteners 510, 500, 520 are adjustable independently to suit the size and shape of the foot of the user, especially when the foot is bandaged at the traumatized foot portion. The upper 5 has left and right end portions 53 which are formed respectively at the left and right flaps and which extend downwardly from the instep straps 51, 50 and the ankle strap 52. The left and right end portions 53 extend to the bottom side of the midsole member 3 so as to be inserted between the bottom side of the midsole member 3 and the top side 11 of the outsole member 1 immediately above the intermediate portion 14 of the latter. Each of the left and right end portions 53 is provided with a loop fastener unit 531 for engaging releasably the hook fastener unit 41 on the bottom side of the midsole member 3.

In assembly, the left and right end portions 53 of the upper 5 are connected to the midsole member 5 by means of the hook and loop fastener units 41, 531, and are disposed at suitable positions on the bottom side of the midsole member 3 according to the scale marks 42 provided thereon. The scale marks 42 serve as reference for adjustment of the size of a space confined by the upper 5 and the midsole member 3 to suit the size of the traumatized human foot.

Figure 4:
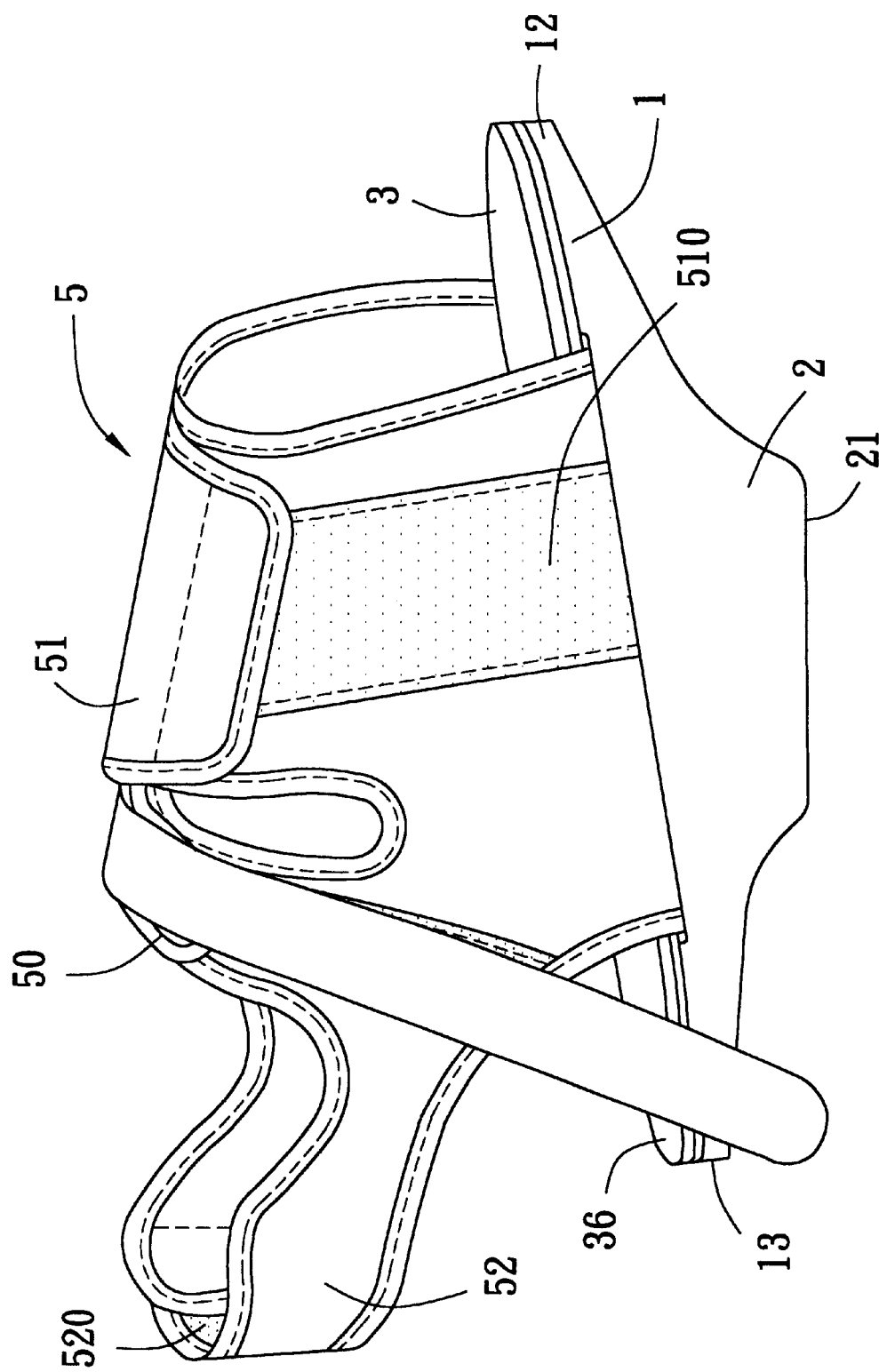
FIG. 4 is a side view of the preferred embodiment in a second mode of use.

In the case the traumatized foot portion of the user is the heel, the post-operation shoe of the present embodiment is assembled to be in a first mode of use, in which the ankle strap 52 is located immediately above a heel portion 36 of the midsole member 3 and the heel portion 36 is located immediately above the second end portion 12 of the outsole member 1, as shown in FIG. 3. Under this condition, the heel portion 36 is raised by the wedge member 2. In the case the traumatized foot portion of the user is the forefoot, the midsole member 3 is first detached from the outsole member 1 by loosening the screws 35. Then, the midsole member 3, with the upper 5 mounted thereon, is turned by an angle of 180° such that the heel portion 36 is located immediate above the first end portion 13 of the outsole member 1 and the ankle strap 52 is located immediately above the heel portion 36 of the midsole member 3, as shown in FIG. 4. In this condition, the forefoot portion of the shoe is raised by the wedge member 2. The adjustment of the shoe of the present embodiment between the first and second modes of use can also be conducted by releasing the upper 5 from the midsole member 3 via the releasable hook and loop fastener units 41, 513, and by turning the upper 5 relative to the midsole member 3 and the outsole member 1 to dispose the ankle strap 52 above a selected one of the first and second end portions 13, 12 of the outsole member 1.

Accordingly, the post-operation shoe of the present invention can be easily detached and assembled for adjustment between the first and second modes of use in order to suit the requirement of the user when the user is traumatized at either the forefoot or the heel. In addition, by securing the wedge member 2 at the intermediate portion 14 of the outsole member 1, enhanced comfort can be attained by the user regardless of whether the traumatized foot portion is the forefoot or the heel. In the preferred embodiment, the bottom side of the midsole member 3 is provided with scale marks 42 which serve as references for adjustment of the size of the shoe. This provides great convenience to the user in the selection of a suitably sized shoe.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claimed:

1. A post-operation shoe comprising:

a sole including an outsole member and a midsole member, said outsole member having first and second end portions which are opposite to each other in a longitudinal direction, and an intermediate portion between said first and second end portions, said midsole overlying and releaseably connected to said outsole member;

a wedge member formed integrally with a bottom side of said outsole member at said intermediate portion, and having a flat bottom end face adapted to be in contact with the ground, said wedge member being tapered in said longitudinal direction so that said second end portion is disposed higher than said first end portion;

an upper including an instep strap, an ankle strap, and left and right end portions extending downward from said instep strap and inserted between said midsole and outsole members; and hook-and-loop fastener means being disposed on said left and right end portions and on one of said midsole and outsole members to releasably mount said upper on said sole, whereby said upper can be positioned to said sole interchangeably between a first position in which said ankle strap is located adjacent to said first end portion, and a second position in which said ankle strap is located adjacent to said second end portion.

2. The post-operation shoe as claimed in claim 1, wherein said bottom side of said midsole member is further provided with scale marks which serve as reference for adjustment of the size of a space confined by said upper and said sole in order to fit the size of a human foot.

3. The post-operation shoe as claimed in claim 2, further comprising screws for fastening detachably said midsole member and said outsole member.

4. The post-operation shoe as claimed in claim 3, wherein said sole has a line of symmetry which passes through said intermediate portion and which is transverse to the longitudinal direction.

5. The post-operation shoe as claimed in claim 1, wherein said hook-and-loop fastener means is disposed on a bottom side of said midsole member.

* * * * *